(12) United States Patent
Bright

(10) Patent No.: US 10,094,215 B2
(45) Date of Patent: Oct. 9, 2018

(54) MUDLOGGING DEVICE WITH DUAL INTERFEROMETERS

(71) Applicant: IBALL INSTRUMENTS LLC, Norman, OK (US)

(72) Inventor: Carl Bright, Harrah, OK (US)

(73) Assignee: IBALL INSTRUMENTS, LLC, Norman, OK (US)

( * ) Notice: Subject to any disclaimer, the term of this patent is extended or adjusted under 35 U.S.C. 154(b) by 260 days.

(21) Appl. No.: 14/831,246

(22) Filed: Aug. 20, 2015

(65) Prior Publication Data

US 2016/0131795 A1    May 12, 2016

Related U.S. Application Data

(60) Provisional application No. 62/078,241, filed on Nov. 11, 2014.

(51) Int. Cl.
*G01V 8/10* (2006.01)
*E21B 49/08* (2006.01)
*G01N 21/3504* (2014.01)
*G01V 8/00* (2006.01)

(52) U.S. Cl.
CPC ....... *E21B 49/086* (2013.01); *G01N 21/3504* (2013.01); *G01V 8/00* (2013.01)

(58) Field of Classification Search
CPC ... G01N 21/45; G01N 21/3504; E21B 49/086
See application file for complete search history.

(56) References Cited

U.S. PATENT DOCUMENTS

| 4,702,604 | A | * | 10/1987 | Achtermann | .......... | G01N 21/45 |
| | | | | | | 356/128 |
| 5,040,895 | A | | 8/1991 | Laurent et al. | | |
| 5,285,261 | A | | 2/1994 | Dumoulin | | |
| 5,589,689 | A | | 12/1996 | Koskinen | | |
| 6,234,030 | B1 | * | 5/2001 | Butler | ...................... | E21B 21/01 |
| | | | | | | 73/195 |
| 6,330,065 | B1 | | 12/2001 | Hill | | |
| 7,421,905 | B2 | * | 9/2008 | Zerwekh | ............ | G01K 11/3206 |
| | | | | | | 374/E11.016 |
| 8,445,841 | B2 | | 5/2013 | Szobota et al. | | |
| 8,941,046 | B2 | | 1/2015 | Freese et al. | | |
| 8,960,294 | B2 | | 2/2015 | Freese et al. | | |
| 2006/0117759 | A1 | * | 6/2006 | Hall | ....................... | E21B 47/011 |
| | | | | | | 62/3.2 |
| 2006/0202122 | A1 | * | 9/2006 | Gunn | ................. | G01N 21/3504 |
| | | | | | | 250/339.13 |
| 2008/0049228 | A1 | * | 2/2008 | Chan | ......................... | G01J 3/26 |
| | | | | | | 356/454 |
| 2008/0186508 | A1 | * | 8/2008 | Kiesel | ....................... | G01J 3/26 |
| | | | | | | 356/519 |
| 2008/0307876 | A1 | * | 12/2008 | Lapierre | ................. | E21B 21/08 |
| | | | | | | 73/152.51 |

(Continued)

*Primary Examiner* — Dominic J Bologna
(74) *Attorney, Agent, or Firm* — Hall Estill Attorneys at Law; Tyler J. Mantooth

(57) ABSTRACT

A mudlogging device may consist of a housing that is positioned above a ground level and proximal a wellbore. The housing can have a first interferometer and a second interferometer that are connected to a common pathway. The duel interferometer configuration may allow a gas sample to be concurrently tested by the respective interferometers.

22 Claims, 4 Drawing Sheets

(56) References Cited

U.S. PATENT DOCUMENTS

| | | | |
|---|---|---|---|
| 2012/0170023 A1* | 7/2012 | Szobota | G01N 21/552 356/51 |
| 2012/0234599 A1* | 9/2012 | Brumboiu | E21B 21/01 175/50 |
| 2012/0250017 A1 | 10/2012 | Morys et al. | |
| 2013/0334412 A1* | 12/2013 | Gunn | G01N 33/2823 250/255 |
| 2014/0139226 A1 | 5/2014 | Jaaskelainen et al. | |
| 2015/0136961 A1* | 5/2015 | Eddy | G01N 21/0332 250/255 |

* cited by examiner

MUDLOGGING DEVICE WITH DUAL INTERFEROMETERS

RELATED APPLICATION

The present application makes a claim of domestic priority to U.S. Provisional Patent Application No. 62/078,241 filed Nov. 11, 2014, the contents of which are hereby incorporated by reference.

SUMMARY

A mudlogging device, in accordance with various embodiments, consists of a housing that is positioned above a ground level and proximal a wellbore. The housing has first and second interferometers that are connected to a common pathway to allow a gas sample to be concurrently tested by the respective interferometers for different hydrocarbons and other gasses that may be present in the gas sample.

DETAILED DESCRIPTION

As hydrocarbon exploration becomes more sophisticated and as drilling speed increases, the rate at which information pertaining to the composition of underground geologic formations is collected becomes increasingly valuable. For instance, fast drilling speeds can inadvertently pass through hydrocarbon containing smaller geologic formations without notice or utilization. Hence, the drilling fluid, also known as mud, can be monitored for the presence of hydrocarbons and other gasses that indicate the type of geologic formations encountered by drilling operations. Although a diverse variety of hydrocarbon sensing configurations may be employed to detect hydrocarbons present in the drilling fluid, existing configurations can be inaccurate and costly in terms of the testing speed. Furthermore, gas detection systems employing multiple gas sensing equipment are nearly non-existent and are too large and slow to be practically viable.

With these issues in mind, various embodiments provide a mudlogging device capable of accurate hydrocarbon and other gas detection in a gas sample relatively quickly with at least two interferometers connected to a common pathway while being positioned within a housing that is located above ground and proximal a wellbore source of the gas sample. The utilization of dual interferometers in an explosion-proof case proximal a wellbore can allow drilling gasses extracted from the mud to be efficiently prepared into a gas sample that is tested for multiple different hydrocarbons and other gasses concurrently due to the dual configuration of the interferometers. With multiple interferometers simultaneously testing a gas sample for hydrocarbons and other gasses, the mudlogging device can also utilize one or more secondary sensors, or sets of sensors, to further test and verify the accuracy of mudlogging operations in the time it would take a single interferometer to accurately detect multiple different specific gasses and hydrocarbons in a gas sample.

Figure 1:
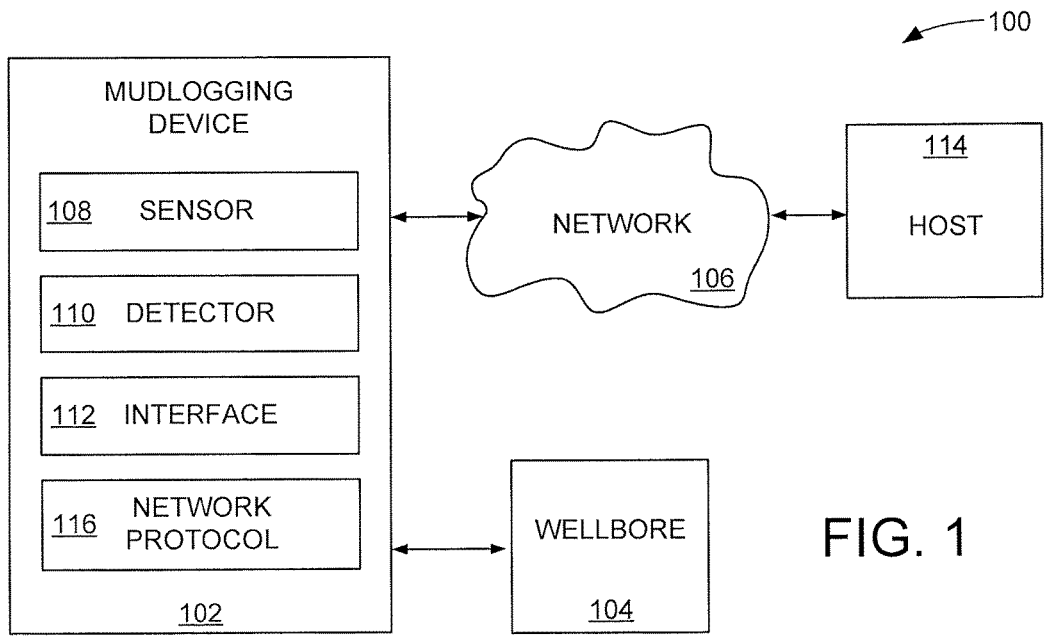
FIG. 1 generally provides a block representation of an example gas detection system in accordance with various embodiments.

FIG. 1 generally provides a block representation of an example hydrocarbon detection system 100 configured in accordance with various embodiments to detect the types and amounts of hydrocarbons or other gasses in drilling mud. The system 100 has a mudlogging device 102 connected to a wellbore 104 and a network 106 through wired and/or wireless connections. While not required or limiting, the mudlogging device 102 can be configured to concurrently engage gasses extracted from the fluid flowing to and from the wellbore 104 and detect various gasses with at least one sensor 108 and detector 110, provide local real-time feedback via an interface 112, and communicate with a remote host 114 via a network protocol 116.

The mudlogging device 102 can connect to and communicate with any number of remote hosts 114 individually and collectively. A remote host 114 can be any number of similar and dissimilar, nodes, servers, processors, and computing devices to transfer data, acquire gas detection algorithms, and operate in conjunction with other devices. The ability to conduct mudlogging operations while connected to a remote host 114 allows the mudlogging device 102 to adapt to changing conditions and respond quickly to system commands, which can optimize the discovery and extraction of hydrocarbons and other gasses, such as crude oil, natural gas, Hydrogen Sulfide, and Helium, from the wellbore 104.

Figure 2:
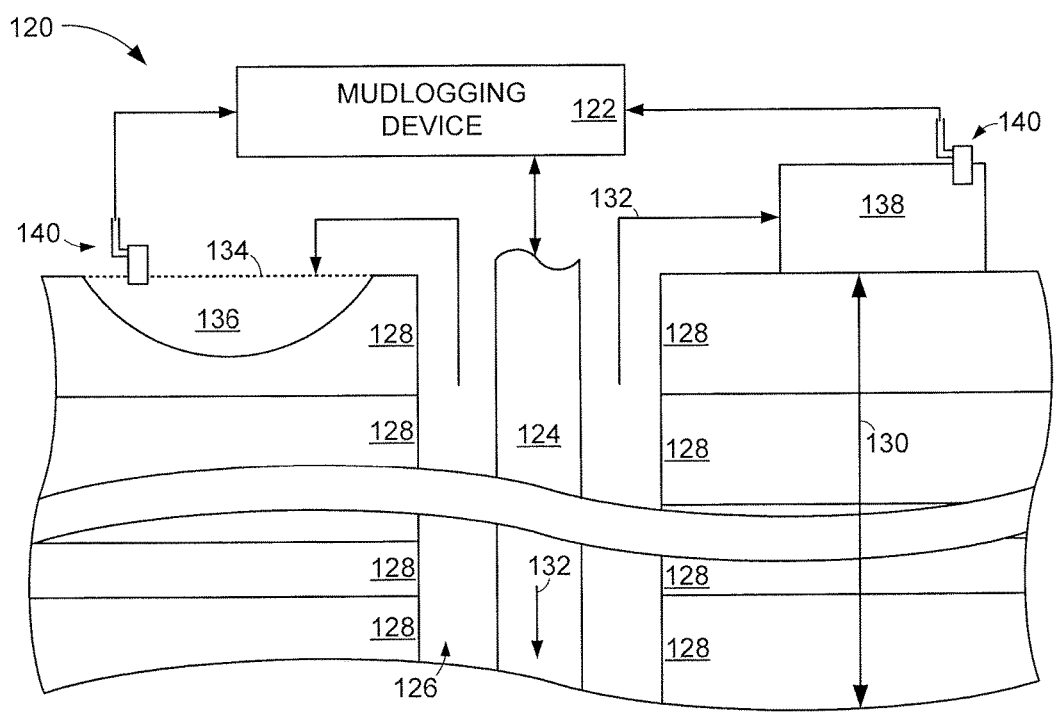
FIG. 2 displays a block representation of an example gas detection environment utilized in accordance with some embodiments.

FIG. 2 displays a block representation of a portion of an example gas extraction environment 120 in which mudlogging can be conducted in accordance with some embodiments to detect various types of gasses. As shown, a mudlogging device 122 is positioned above ground. Piping 124 may be drilling pipe and conduit while the wellbore 126 may be exposed to a plurality of different geological formations 128, such as sand, limestone, shale, and granite. It is to be understood that the piping 124 and wellbore 126 can be any depth 130 and have constant or varying amounts of drilling fluid 132, such as drilling mud, flowing into and out of the wellbore 126.

The position of the mudlogging device 122 proximal the wellbore 126 and above ground level 134 allows the entirety of the geological formations 128 to be evaluated with minimal loss of entrapped hydrocarbons. That is, positioning the mudlogging device 122 close to the wellbore reduces and eliminates the loss of hydrocarbons and other gasses from drilling mud. The position of the mudlogging device 122 can also allow for efficient passage of drilling gasses extracted from the mud 132 from the wellbore 126 through an open air pit 136 and/or a closed tank 138 to the mudlogging device 122 via one or more extractors 140. It is noted that the mudlogging device 122 can be configured to engage and measure the type and amount of hydrocarbons present in any location within the wellbore 126, such as outside and inside the drilling piping 124 utilizing an extractor 140.

In some embodiments, the mudlogging device 122 is positioned above ground level 132 and within a certain distance from the wellbore 126, such as 50 feet or less, to separate the mudlogging sensing equipment, such as sensor 108 and detector 110 of FIG. 1, from the immediate harsh environment of the wellbore 126. That is, hydrocarbon and other gas detecting equipment is positioned outside of the wellbore 126 to ensure the heat, vibration, and debris often present in the wellbore 126 does not degrade or corrupt the operation of the mudlogging device 122. However, it is contemplated that the mudlogging device 122 senses conditions in the wellbore 126, such as temperature, pressure, and fluid density, which can be selectively utilized to detect hydrocarbons and other gasses entrapped in the drilling mud.

Figure 3:
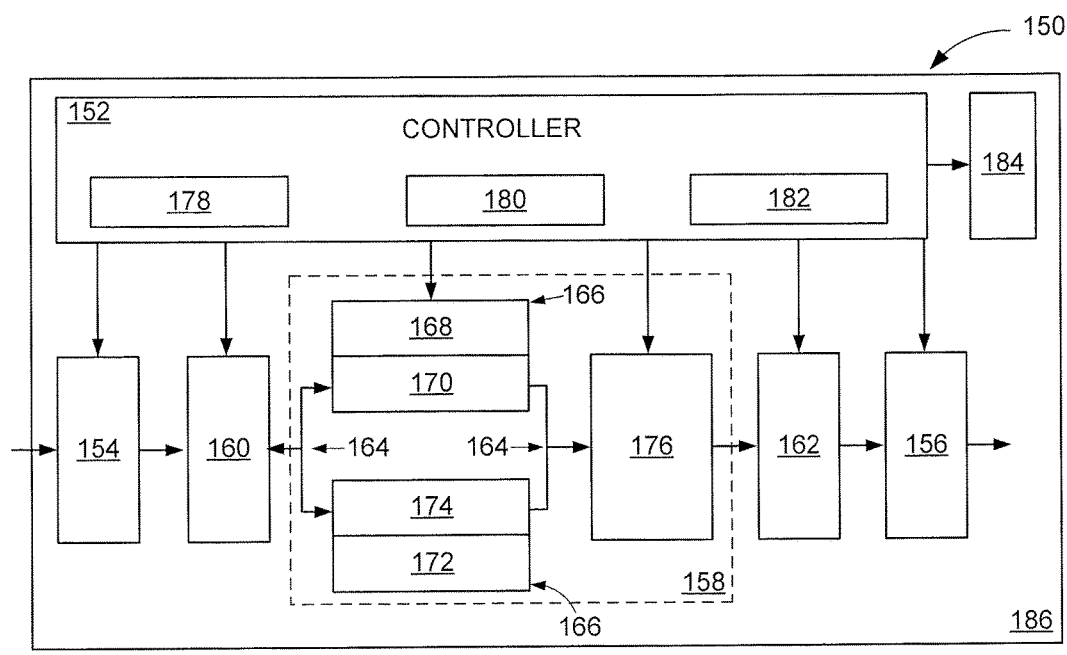
FIG. 3 shows a block representation of an example mudlogging device utilized in accordance with assorted embodiments.

FIG. 3 illustrates a block representation of a portion of an example mudlogging system 150 arranged in accordance with various embodiments to provide optimized hydrocarbon detection accuracy and speed. A common housing, such as an explosion-proof case, can contain at least one controller 152 connected to one or more gas pumps or compressors 154 that are downstream from one or more gas separators, such as extractor 140 of FIG. 2. The upstream 154 and downstream 156 pump/compressors can produce pressure differentials that move a gas sample into a testing region 158 that is selectively opened and closed via upstream 160 and downstream 162 solenoids. In operation, the upstream pump/compressor 154 and solenoid 160 can operate in concert with the downstream solenoid 162 and pump/compressor 156 to receive, test, and eject a gas sample to and from the test region 158.

Although not required or limiting, the testing region 158 consists, according to various embodiments, of a common pathway 164, such as a pipe, tube, or hose, to which first and second testing modules 166 are connected together in a configuration that can be characterized as parallel. For the purposes of this disclosure, the term "parallel" is meant as branches of the common pathway 164 that have a matching length. The testing module 166 parallel configuration is contrasted connecting multiple testing modules in series, which would involve the successive positioning of one testing module 166 upstream of the other module. To further illustrate the difference between parallel and series testing configurations, the parallel arrangement shown in FIG. 3 allows a gas sample to be concurrently tested by each testing module 166 without first passing through an upstream testing module.

Each testing module 166 can be connected to the controller 152 and directed by the controller 152 to test for similar or dissimilar types of hydrocarbons and other gasses. For example, a first testing module 166 can have an interferometer 168 connected to a gas cell 170 to allow optical testing for one or more specific hydrocarbons, such as methane and butane, while a second testing module 166 has an interferometer 172 and gas cell 174 arranged to allow optical testing for a one or more different hydrocarbons, such as octane and propane. Further, the utilization of dual interferometers allows one interferometer 168 detecting different hydrocarbons and the other interferometer 172 detects a different set of gasses, such as Helium. The ability to tune the respective interferometers 168 and 172 to test for different hydrocarbons allows the controller 152 to simultaneously evaluate a gas sample for the presence and amount of hydrocarbons and other gasses, which decreases overall testing time.

The controller 152 can continuously, sporadically, routinely, and randomly monitor the testing region 158, as specifically the common pathway 164, for various conditions, such as pressure and temperature, with one or more sensors to ensure the testing conditions for the testing modules 166 is within defined parameters to provide accurate readings. In some embodiments, the controller 152 compares readings within the testing region 158 with readings from outside the testing region 158 to evaluate and determine the status of the gas sample, such as the presence of unwanted liquids and solids.

The testing region 158 and common pathway 164 may each consist of one or more secondary sensors 176 that access the common pathway 164 and gas sample to provide measurements that complement the testing of the gas sample and operation of the mudlogging device 150. For example, the secondary sensors 176 may consist of one or more additional testing equipment, such as an infrared gas testing means, a pellistor, Oxygen, $H_2S$, or a mass spectrometer. The secondary sensors 176 may also consist of environmental testing equipment, such as temperature and pressure sensors, as well as diagnostic equipment, such as voltmeters and vibration sensors. The ability to tune the secondary sensors 176 to include any number and type of testing equipment can correspond with increased mudlogging intelligence the identifies current conditions and allows the controller 152 to proactively address potential testing and operation issues.

The controller 152 may have one or more different kinds of processors 178, memories 180, and communications 182 means that can log, store, and transfer information to and from the testing region 158 to remote locations, such as remote hosts, nodes, and servers. The processing means 178 can consist of one or more microprocessors and application specific integrated circuits (ASIC) while the memory means 180 consists of one or more kinds of volatile and non-volatile rotating and/or solid-state data storage means. The communications 182 capabilities of the controller 152 can allow at least cellular, broadband wireless, radio, and specific frequency data transfer that operate individually and concurrently. For example, a 900 MHz fixed frequency may operate simultaneously with cellular and Wi-Fi protocol.

The controller 152 can direct one or more case diagnostic equipment, such as a temperature 184 sensor and/or a vibration sensor, that monitors conditions inside the testing case 186 that houses the pumps 154 and 156, solenoids 160 and 162, testing region 158, and controller 152. Monitoring the conditions of the testing case 186 allows predetermined temperatures, pressures, and vibrations to be maintained to ensure optimized testing conditions for the testing modules 166 and secondary sensors 176. Various embodiments allow the controller 152 to conduct maintenance and corrective operations on the common pathway 166 with the upstream 154 and downstream 156 compressor/pumps in association with the solenoids 160 and 162. For example, the pumps 154 and 156 can conduct blow-back operations where gas, such as outside air, is forced in a reverse flow through the common pathway 164 to clear the testing region 158 of occlusions, condensation, and gas pockets.

Although not required or limiting, the tuned configuration of the mudlogging device 150 allows for a diverse variety of gas sample testing and evaluations to be conducted. The ability to tune the testing modules 166 to incorporate various types of testing means allows the parallel configuration of the testing modules 166 to concurrently test for different parameters that quickly and accurately identify a range of different hydrocarbon and other gas types and amounts in the gas sample. In accordance with some embodiments, differently tuned interferometers 168 and 172 test for diverse hydrocarbons via optical analysis through the respective gas cells 170 and 174. It is contemplated that different types of interferometers are utilized in the respective testing modules 166, such as Michelson, Fabry-Perot, and Linnik types.

Figure 4:
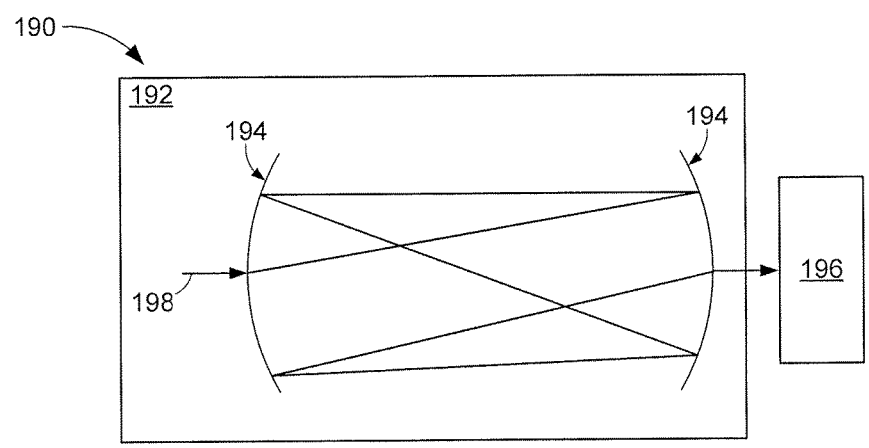
FIG. 4 is a block representation of an example gas detector configured in accordance with various embodiments.

FIG. 4 illustrates a block representation of an example testing module 190 constructed and operated in accordance with some embodiments. The testing module 190 has a gas cell 192 that incorporates at least two reflecting surfaces 194 that operate in conjunction with one or more detectors 196 as an interferometer. As shown, the interferometer can pass an optical beam 198 through a gas sample contained in the gas cell 192. The optical beam 198 bounces between the reflective surfaces 194 and only optical wavelengths within a tuned range escape and are sensed by the detector 196. The tuned configuration of reflective surfaces 194, such as the size, separation distance, and wavelength range that escapes to the detector 196 allows the testing module 190 to identify a diverse variety of gas compositions.

Various embodiments can utilize different infrared (IR) frequency ranges, such as near IR, mid IR, and far IR, to accurately detect specific gas molecules, such as methane or propane. The optical evaluation of a gas sample in the gas cell 192 by the interferometer is non-destructive and allows for subsequent gas sample testing and evaluation. As a non-limiting example, parallel interferometers tuned to detect different hydrocarbons pass a gas sample to a secondary hydrocarbon testing means, such as a mass spectrometer, that subsequently verifies the measurements of the respective interferometers.

Figure 5:
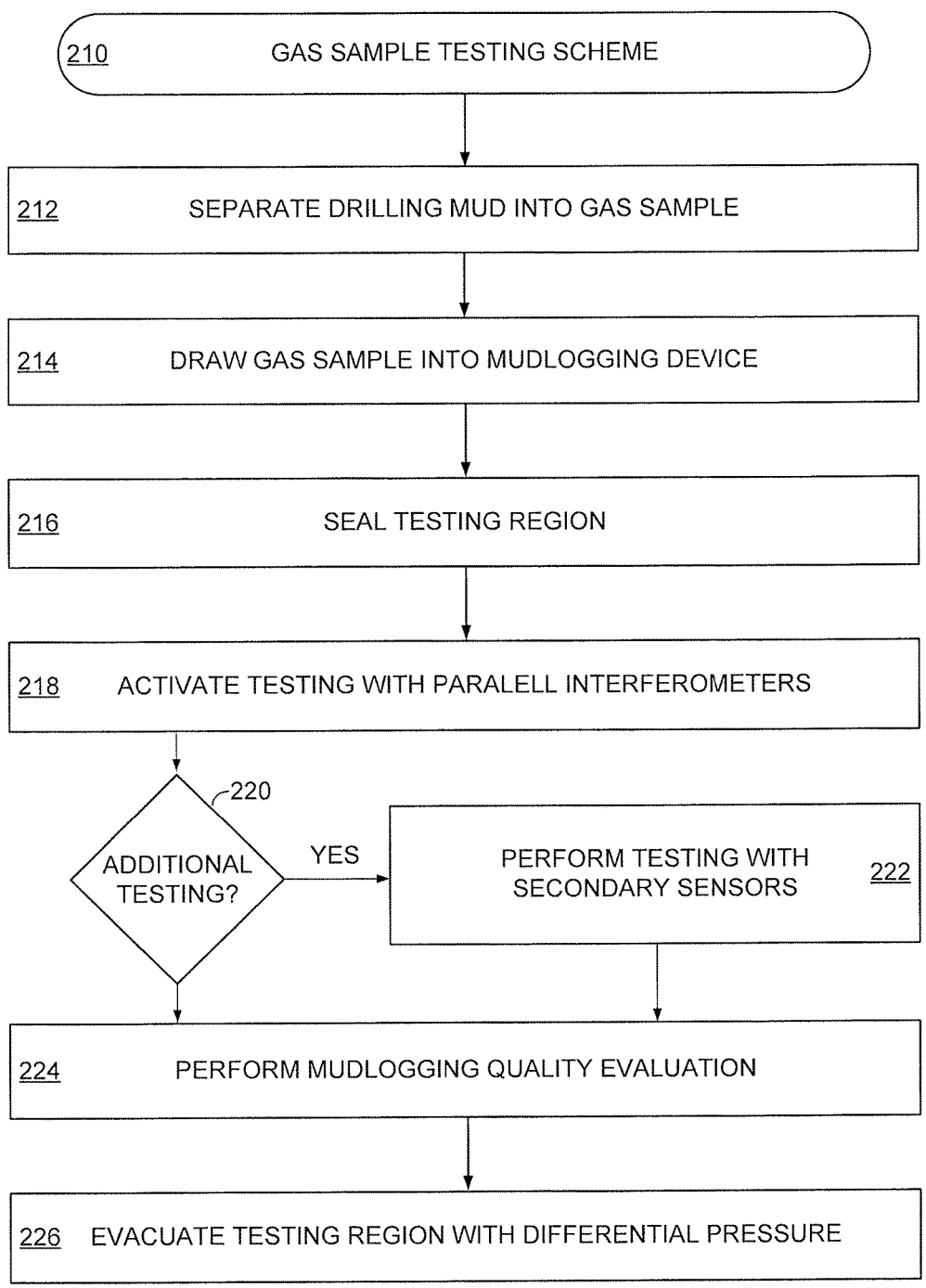
FIG. 5 plots an example mudlogging prediction scheme performed in accordance with some embodiments.

With multiple gas testing means incorporated into a mudlogging device, a variety of different testing operations and sequences can be selectively utilized to provide the constituent hydrocarbon and other gas types and amounts present in a gas sample. FIG. 5 is an example gas sample testing scheme 210 performed in accordance with some embodiments to detect the presence of hydrocarbons and other gasses in a gas sample separated from drilling mud. The scheme 210 begins by separating drilling mud to provide a gas sample in step 212. The separation may occur naturally, such as with gas rising to the top of a tank, or forcibly, such as with a centrifuge or gas extraction device.

The separated gas sample is drawn into a mudlogging device in step 214 by creating a pressure differential that may involve the activation of one or more solenoids. It is contemplated that the gas sample is filtered in step 214 by at least one filtering means, such as a screen or filter. Once the gas sample pressurizes a testing region of the mudlogging device to a predetermined pressure, step 216 seals the testing region with upstream and downstream solenoids prior to step 218 concurrently activating testing modules connected to a common pathway in parallel.

While the gas sample is pressurized in the testing region, decision 220 can evaluate whether additional sensing is to take place with one or more secondary sensors. Decision 220 may consider at least the speed, testing conditions, accuracy, and testing age of the testing modules to determine if secondary sensors are to be employed to verify and/or redundantly test the gas sample. If additional sensing is to be conducted, step 222 performs such testing with at least one secondary sensor, which may include re-testing the gas sample with the original testing module.

In the event no additional sensing is to take place, or after additional testing is completed in step 222, step 224 utilizes at least one secondary sensor to perform mudlogging quality evaluations. Such evaluations may involve performing status tests for individual and collective aspects of the testing region. For instance, step 224 may employ at least one secondary sensor to confirm an error from a mudlogging device sensor, such as a temperature sensor, and verify a pressure of the testing region during testing. The quality evaluations of step 224 can serve to defeat a bad reading or sensor and provide accurate hydrocarbon detection. That is, step 224 can allow a mudlogging device to provide accurate testing measurements instead of an error as a result of status tests identifying an erroneous, inaccurate, or otherwise inconsequential sensor reading.

Regardless of whether step 224 corrects, verifies, or ignores bad or inaccurate sensor readings, step 226 subsequently evacuates the testing region of the gas sample through an exhaust port of the mudlogging case by creating a pressure differential. It is contemplated that scheme 210 is conducted with local and remote controllers that are connected via one or more wired and/or wireless communication means. The ability to adapt to changing environmental conditions, such as temperature and vibration, to quickly and accurately test for a variety of different hydrocarbons in a gas sample allows scheme 210 to provide optimized mudlogging operations.

Figure 6:
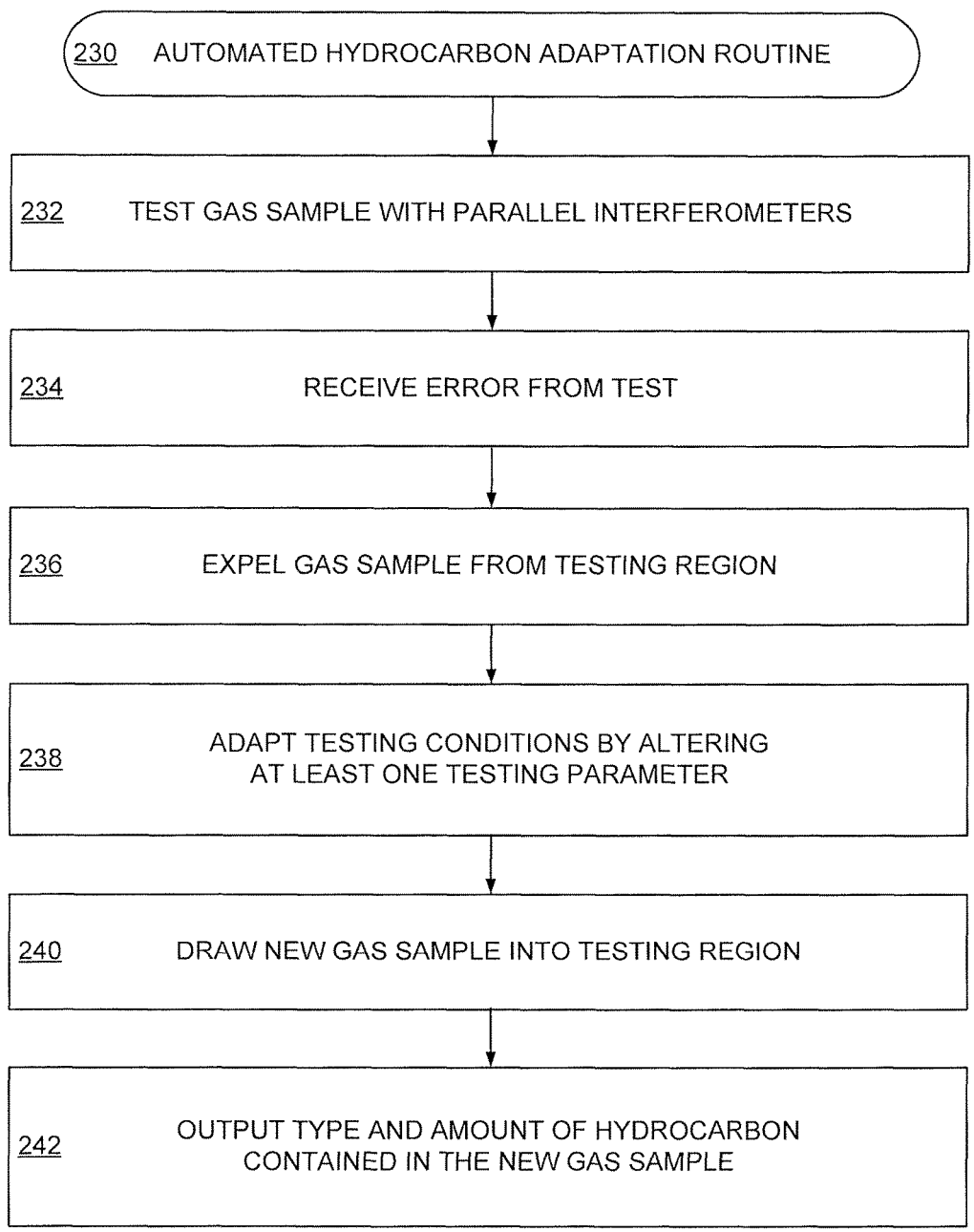
FIG. 6 maps an example gas mudlogging routine carried out in accordance with assorted embodiments.

FIG. 6 conveys an example automated hydrocarbon adaptation routine 230 that is carried out in accordance with some embodiments to quickly and accurately detect constituent hydrocarbons and other gasses in drilling mud. Initially, step 232 tests a gas sample, which may be conducted with scheme 210 of FIG. 5. As a result of step 232, an error is received by a local or remote controller in step 234 that triggers the expulsion of the gas sample from the testing region in step 236. The error from step 234 can be evaluated by at least one controller to adapt the mudlogging system to correct the error.

While any number, type, and sequence of adaptations can be conducted in step 238, various embodiments tune the pump/compressor speeds, pump/compressor direction, system temperature, common pathway pressure, and testing time to increase the accuracy of the previous gas sample testing. That is, step 238 can reactively change testing conditions in response to the error of step 234 or proactively change testing parameters to decrease the risk of future testing errors. Step 238 can rely on logged testing data, any number of predictive algorithms, and testing models to predict the occurrence of future errors and the corrective adaptations needed to mitigate the risk of an error occurring.

The execution of the adaptations in step 238 advances routine 230 to step 240 where a new gas sample is drawn in to the testing region and tested. In some embodiments, the number and/or type of testing means of step 240 are different than employed in step 232. For example, multiple additional secondary sensors may be utilized in step 240 to verify interferometer readings, identify potentially bad sensors, and ensure proper testing conditions were present during testing. A secondary process may actually re-calibrate other sensors based on any error detected. As a result of the adapted testing in step 240, step 242 outputs the type and amount of hydrocarbons and other gasses in a gas sample that is compared to the results of step 232 to help identify future testing adaptations that may optimize the speed and accuracy of routine 230.

Through the various aspects of scheme 210 and routine 230, a gas sample originating in drilling mud can be tested to identify the type and amount of hydrocarbons and other gasses contained therein. The ability to tune the number, type, and sequence of testing equipment in a mudlogging device allows for testing adaptations that allow errors and inaccurate readings to be overcome. By encompassing controlling, testing, and operational equipment in a single mobile case, the mudlogging device can be easily transported and set up proximal a wellbore. The various wireless communications capabilities of the mobile mudlogging device can provide real-time hydrocarbon testing and environmental adaptations that can result in optimized downhole drilling operations due to the increased knowledge of the type of geologic formation providing hydrocarbons to the drilling mud.

What is claimed is:

1. An apparatus comprising a housing positioned above a ground level and separated from a wellbore, the housing containing first and second interferometers connected to a common pathway in a single container to allow a single gas sample to be concurrently tested by the respective interferometers, each interferometer connected to a gas cell comprising reflecting surfaces configured to optically detect gas molecules, the first interferometer having a first pair of reflecting surfaces configured to detect different gas molecules in combination with a first detector than a second pair of reflecting surfaces of the second interferometer in combination with a second detector.

2. The apparatus of claim 1, wherein the first and second interferometers are respectively connected to different first and second gas cells.

3. The apparatus of claim 2, wherein reflecting surfaces of the respective gas cells are oriented to allow only predetermined wavelengths to escape to the respective detectors.

4. The apparatus of claim 2, wherein first gas cell is configured to detect hydrocarbon based gasses with the first detector, the second gas cell is configured to detect non-hydrocarbon based gasses with the second detector.

5. The apparatus of claim 2, wherein the first and second gas cells are respectively configured to detect different types of gasses with the respective first and second detectors.

6. The apparatus of claim 1, wherein the reflective surfaces of the first and second gas cells are each curved to provide different ranges of optical wavelengths to the respective detectors.

7. The apparatus of claim 1, wherein the housing is an explosion-proof case.

8. The apparatus of claim 1, wherein a gas extractor is positioned upstream from the housing and is configured to extract gasses entrapped in mud originating in the wellbore.

9. The apparatus of claim 1, wherein the single container is separated from the wellbore and is positioned 50 feet or less from the wellbore.

10. The apparatus of claim 1, wherein the first and second interferometers are connected in parallel with the common pathway.

11. An apparatus comprising:
a housing having a controller, the housing positioned proximal to and outside of a wellbore;
a gas separator providing an inlet of the housing a gas sample;
a first interferometer positioned in the housing and configured to test for hydrocarbon based gasses, the first interferometer comprising a first gas cell and a first detector, a first pair of reflecting surfaces positioned within the first gas cell and connected to the first detector; and
a second interferometer positioned in the housing and connected to a common pathway with the first interferometer, the second interferometer comprising a second gas cell and a second detector, configured to test for a gas other than the hydrocarbons concurrently while the first interferometer tests for the hydrocarbon based gasses, a second pair of reflecting surfaces positioned within the second gas cell.

12. The apparatus of claim 11, wherein a secondary sensor is positioned within the housing and connected downstream from the first and second interferometers on the common pathway.

13. The apparatus of claim 12, wherein the secondary sensor comprises a temperature sensor.

14. The apparatus of claim 12, wherein the secondary sensor comprises a mass spectrometer.

15. The apparatus of claim 12, wherein the secondary sensor comprises an oxygen sensor.

16. The apparatus of claim 12, wherein the secondary sensor comprises an infrared gas testing means.

17. A method comprising:
positioning first and second interferometers in a housing, each interferometer comprising a pair of reflecting surfaces positioned in a gas cell and connected to a detector ,the first interferometer configured to detect a first amount of a first gas molecule, the second interferometer configured to detect a second amount of a second gas molecule, the first and second gas molecules being different;
connecting the first and second interferometers to a common pathway; and
detecting the first and second gas molecules in a gas sample concurrently by the respective interferometers.

18. The method of claim 17, wherein upstream and downstream compressors are positioned within the housing and draw sample gas into a gas cell connected to the each interferometer simultaneously.

19. The method of claim 17, wherein the first gas molecule is a hydrocarbon based gas and the second gas molecule is a non-hydrocarbon based gas.

20. The method of claim 17, wherein at least one secondary sensor positioned downstream of the interferometers tests for the presence and amount of gasses to verify a previous result of at least one interferometer before the gas sample is evacuated from the housing.

21. The method of claim 17, wherein first and second solenoids are connected to the common pathway and selectively flow gas through the common pathway to clear obstructions from the housing.

22. The method of claim 17, wherein a controller of the housing controls an internal temperature of the housing with a thermoelectric peltier device.

* * * * *